June 2, 1942. R. L. BYRUM Plant Pat. 525
ROSE PLANT
Filed Nov. 15, 1941
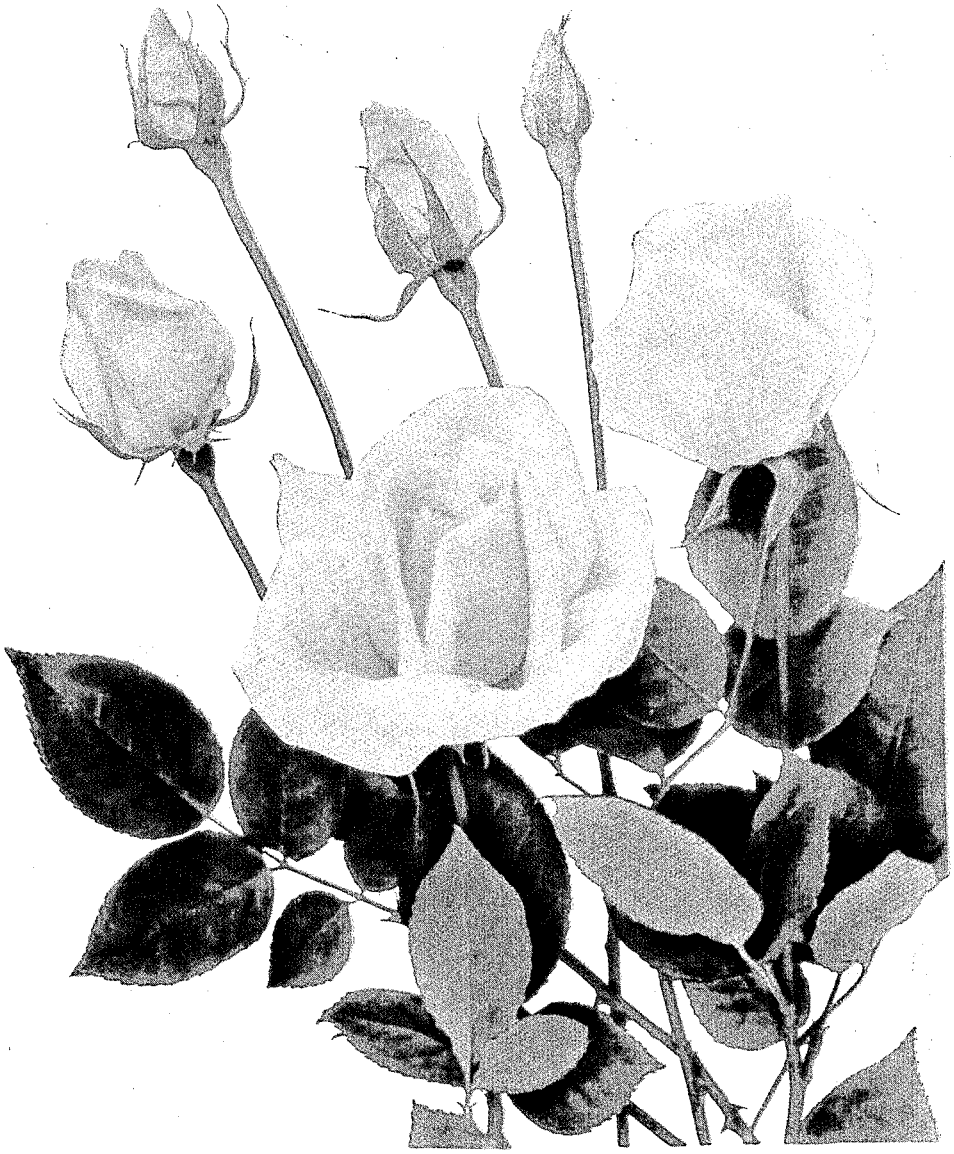
Inventor
R. L. Byrum
By Robert Robb
attorney Patented June 2, 1942

Plant Pat. 525

UNITED STATES PATENT OFFICE

525

ROSE PLANT

Roy L. Byrum, Richmond, Ind., assignor to Joseph H. Hill Company, Richmond, Ind., a corporation of Indiana Application November 15, 1941, Serial No. 419,350

1 Claim. (Cl. 47—61)

The present invention relates to a new and distinct variety of hybrid tea rose, originating from a cross between the known varieties "Joanna Hill" and "R. M. S. Queen Mary" (Plant Patent No. 249) to obtain improvements over each.

As a result, I have produced a rose similar in growth, shape of bud and bloom to "Captain Glisson" (Plant Patent No. 155), but having more similarity in texture of foliage to "R. M. S. Queen Mary," above referred to.

Its primary distinguishing features reside in the color of the flowers, darker than that of either of its parents, its great productiveness, the blooms coming on long stems from a cut without resorting to "pinching," and the resistance to mildew and blackspot. The great productiveness above referred to was based upon cutting records for a period of years in comparison with standard varieties, and the resistance to mildew and blackspot characteristic was determined by growing the present variety next to a variety on which blackspot has been present throughout the growing season. On the other side of this new variety is one which has had mildew at various times during the season. However, the present variety has been clean the entire time under identical growing and disease preventive conditions. These distinguishing characteristics have been found to hold true through succeeding propagations by the usual methods tried of cuttings, graftings and buddings.

The color terminology herein employed is in accord with Ridgway's Color Standards where indicated by plate numbers, otherwise with general dictionary meaning.

The following is a detailed description of this new variety of rose:

Type: Bush; greenhouse; seedling; for cut flowers.

Class: Hybrid tea.

Breeding: Seedling.

*Seed Parent.*—"Joanna Hill."

*Pollen Parent.*—"R. M. S. Queen Mary."

*Flower*

Locality where grown: Richmond, Indiana.

Flowers borne: Singly to stem; in irregular cluster; on strong, long stems.

Quantity of bloom: Abundant in greenhouse.

Continuity: Continuous.

Fragrance: Moderate; tea.

Bud:

*Peduncle.*—Long; medium heavy; erect; stiff; yellowish; green; entirely smooth; few green hairs.

*Before calyx breaks.*—*Size*—medium.

*Form*—Long, pointed with a conspicuous neck; with foliaceous appendages on the surface of the bud with much-cut, bristle-like foliaceous parts extending beyond the tip of the bud equal to three-fourths or more of its length.

*As calyx breaks.*—*Color*—Light Coral Red, Plate XIII.

*As first petal opens.*—*Size*—medium large.

*Form*—very long pointed. *Color:* outside—base is Pale Lemon Yelow, Plate IV, shading to Coral Pink at end of petal, Plate XIII; inside—base is Lemon Chrome, Plate IV, shading to Light Orange Yellow, Plate III, striped with Coral Pink, Plate XIII.

*Opening.*—Opens up well.

Bloom:

*Size, when fully open.*—Large; four to five inches.

*Petalage.*—Double; from twenty-five to thirty petals; arranged irregularly.

*Form.*—Globular at first, becoming flat, open; petals remaining at first loosely rolled outward; becoming later, at maturity, very loosely rolled outward.

Petals: Thick; soft; with inside and outside, shiny, satiny.

*Shape.*—Outside—obovate with apex flat with one notch. Intermediate—obovate with apex flat with one notch. Inside—obovate; irregular with apex flat with one notch.

This description of a newly opened flower was made from a rose grown in a greenhouse during the month of September, 1941, at Richmond, Indiana:

*Color.*—Outside petal: outside surface—base is Pale Lemon Yellow, Plate IV, shading to White with slight covering of Pale Rhodonite Pink, Plate XXXVIII; inside surface—base is Lemon Chrome, Plate IV, shading to White. Intermediate petal: outside surface—base is Lemon Yellow, Plate IV, shading to Flesh Pink, Plate XIII; inside surface—base is Lemon Chrome, Plate IV, shading to Light Buff, Plate XV. Inner petal: outside surface—base is Lemon Yellow, Plate IV, shading to Flesh Color, Plate XIV; some petals have streak of Lemon Yellow through center from base to tip; inside surface—base is Lemon Chrome, Plate IV, shading to Capucine Buff, Plate III.

This description was made from a rose that was open for three days in a greenhouse, during the month of September, 1941, at Richmond, Indiana:

*Color.*—Outside petal: outside surface—base is Lemon Yellow, Plate IV, shading to White with slight covering of Pale Rhodonite Pink, Plate XXXVIII; inside surface—base is Lemon Yellow, Plate IV, shading to almost White. Inside petal: outside surface—base is Lemon Yellow, Plate IV, shading to White with slight covering of Pale Rhodonite Pink, Plate XXXVIII; inside surface—base is Lemon Yellow, Plate IV, shading to almost White.

*General color effect.*—Newly opened flower—Capucine Buff, Plate III. Three days open—Pale Pinkish Buff, Plate XXIX.

*Behavior.*—Persist; affected by hot weather, fading lighter.

*Flower longevity.*—As cut roses grown in greenhouse kept at living-room temperature, five days in September.

*Reproductive organs*

Stamens: Many; arranged regularly about pistils.

Filaments: Long; yellow; most with anthers.

Anthers: Medium large; reddish; all open at once.

Pollen: Very abundant; gold.

Pistils: Many.

Styles: Uneven; medium long; medium heavy; bunched.

Stigma: White.

Ovaries: All enclosed in calyx.

Sepals: Permanent; moderately long; spear-shaped; curled;

*Color.*—Inside — Chromium Green, Plate XXXII, with fuzz on surface. Outside—Chromium Green, Plate XXXII.

Seeds: No seeds available, September, 1941.

*Plant*

Foliage:

*Leaves.*—Compound of five to seven; very abundant; large; heavy; leathery; wrinkled.

*Leaflets.*—*Shape*—ovoid, with apex acute; base obtuse; margin simply serrate.

*Color.*—*Mature*: upper surface—Dark Dull Yellow Green, Plate XXXII; under surface—Bice Green, Plate XVII. *Young:* upper surface—Deep Dull Yellow-Green, (1), Plate XXXII, with slight bronze tinge; under surface—Light Bice Green, Plate XVII, with slight bronze tinge.

*Rachis.*—Heavy. Upper side — grooved; hairy. Under side—smooth; prickly.

*Stipules*: Short; medium wide; with moderately short points turning out at an angle of less than 45°.

*Disease.*—Resistant to mildew and blackspot.

Growth:

*Habit.*—Bush; upright; much branched.

*Growth.*—Free; vigorous.

*Canes.*—Heavy.

*Main stems.*—Dull green streaked with rust. *Thorns*—several; medium long; hooked downward; with short broad base. *Prickles*—few; brown. *Hairs*—none.

*Branches.*—Bright green. *Thorns*—several; medium long; hooked downward; with short broad base. *Prickles*—few; green. *Hairs*—none.

*New shoots.*—Dull bronze red. *Thorns*—several; medium long; hooked downward; with short broad base. *Prickles*—few; reddish. *Hairs*—none.

I claim:

A new and distinct variety of hybrid tea rose, characterized as to novelty by the color combination of its blossoms, its great productiveness, the growth of single blossoms on strong, long stems, and its disease resistance, substantially as shown and described.

ROY L. BYRUM.